(12) United States Patent
Greenberg

(10) Patent No.: US 7,210,881 B2
(45) Date of Patent: May 1, 2007

(54) SLEEVED STOP FOR A DRILL BIT

(76) Inventor: Alex M. Greenberg, 2373 Broadway, New York, NY (US) 10024

( * ) Notice: Subject to any disclaimer, the term of this patent is extended or adjusted under 35 U.S.C. 154(b) by 51 days.

(21) Appl. No.: 10/748,338

(22) Filed: Dec. 30, 2003

(65) Prior Publication Data
US 2005/0147478 A1    Jul. 7, 2005

(51) Int. Cl.
*B23B 51/02*    (2006.01)
(52) U.S. Cl. .................. 408/202; 408/80; 408/110; 408/241 S
(58) Field of Classification Search .................. 408/14, 408/79, 80, 97, 110, 112, 113, 202, 241 S
See application file for complete search history.

(56) References Cited

U.S. PATENT DOCUMENTS

| | | | |
|---|---|---|---|
| 1,439,567 A * | 12/1922 | Maupin ...................... 408/56 |
| 2,216,988 A * | 10/1940 | Schmidt ..................... 408/113 |
| 2,231,864 A * | 2/1941 | Abel .......................... 408/202 |
| 2,608,114 A * | 8/1952 | Martin et al. ................ 408/112 |
| 2,704,011 A * | 3/1955 | Frauenberger .............. 409/136 |
| 2,794,353 A * | 6/1957 | Bashlow et al. ............ 408/113 |
| 3,083,593 A * | 4/1963 | Cutter ..................... 408/241 R |
| 3,191,462 A * | 6/1965 | Plunske ........................ 408/80 |
| 4,592,257 A * | 6/1986 | Durr ........................... 81/429 |
| 4,637,539 A * | 1/1987 | Turcott et al. ............... 227/156 |
| 4,705,436 A * | 11/1987 | Robertson .................. 408/72 R |
| 4,710,075 A | 12/1987 | Davison |
| 4,752,158 A * | 6/1988 | Riley .......................... 408/14 |
| 4,877,359 A * | 10/1989 | Kolacek ...................... 409/218 |
| 5,078,552 A | 1/1992 | Albel |
| 5,080,535 A * | 1/1992 | Hirano ....................... 408/67 |
| 5,147,164 A | 9/1992 | Fraver |
| 5,152,792 A | 10/1992 | Watkins et al. |
| 5,382,120 A * | 1/1995 | Parsons ....................... 408/16 |
| 5,669,915 A * | 9/1997 | Caspar et al. ................. 606/96 |
| 5,746,551 A * | 5/1998 | Skaggs ....................... 408/1 R |
| 5,746,552 A * | 5/1998 | Tsui et al. ................. 408/72 B |
| 5,810,828 A * | 9/1998 | Lightman et al. .............. 606/80 |
| 5,893,684 A * | 4/1999 | Skaggs ....................... 408/1 R |
| 5,947,654 A * | 9/1999 | Blankenship et al. ...... 408/72 B |
| 6,063,088 A | 5/2000 | Winslow |
| 6,110,178 A * | 8/2000 | Zech et al. .................... 606/96 |
| 6,203,253 B1 * | 3/2001 | Perrault ....................... 408/84 |
| 6,514,258 B1 * | 2/2003 | Brown et al. .................. 606/80 |
| 6,543,971 B2 * | 4/2003 | Mawhinney ................. 408/202 |
| 6,722,447 B2 * | 4/2004 | Stepan et al. .................. 173/1 |
| 6,739,872 B1 * | 5/2004 | Turri ........................... 433/75 |
| 6,913,427 B2 * | 7/2005 | Erickson et al. .............. 408/95 |
| 6,951,562 B2 * | 10/2005 | Zwirnmann .................. 606/80 |
| 2003/0133764 A1 * | 7/2003 | Erickson et al. .............. 408/97 |
| 2005/0013674 A1 * | 1/2005 | Vidal ........................... 408/67 |

* cited by examiner

FOREIGN PATENT DOCUMENTS

EP    1671752 A1 *    6/2006

*Primary Examiner*—Monica Carter
*Assistant Examiner*—Michael W. Talbot
(74) *Attorney, Agent, or Firm*—Cohen Pontani Lieberman & Pavane LLP

(57) ABSTRACT

A stop for use with an electric drill bit, the stop having at least one threaded sleeve for positioning the stop relative to a surface into which the drill bit will extend. The stop may have both an inner and an outer sleeve. The sleeves are mounted coaxially, one inside the other about the drill bit. One of the sleeves, preferably the inner sleeve, provides coarse adjustment of the position of the shoulder relative to the tip of the bit, while the other, preferably the outer sleeve, provides fine adjustment of the position of the shoulder relative to the top of the bit.

7 Claims, 5 Drawing Sheets

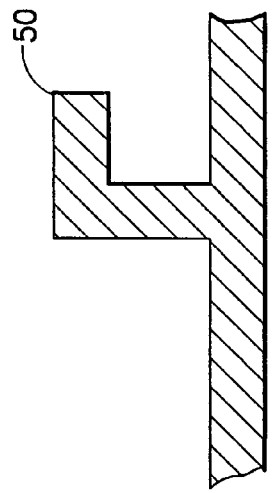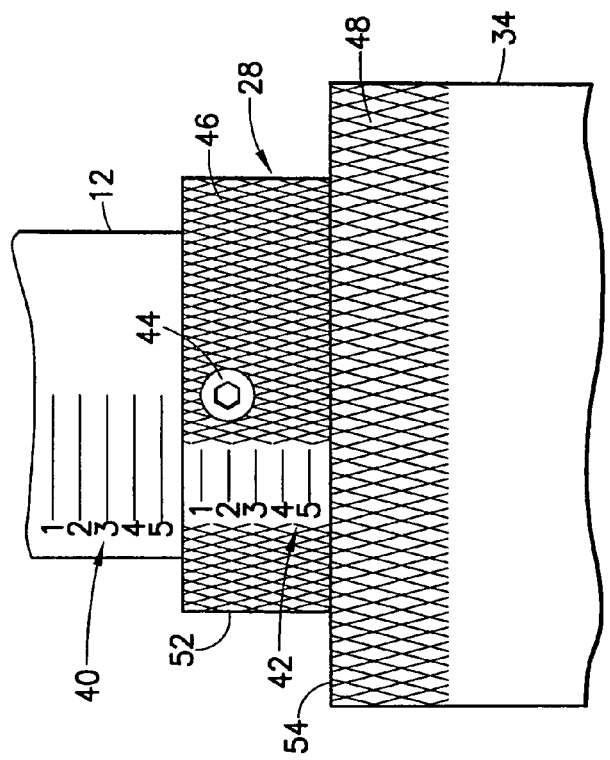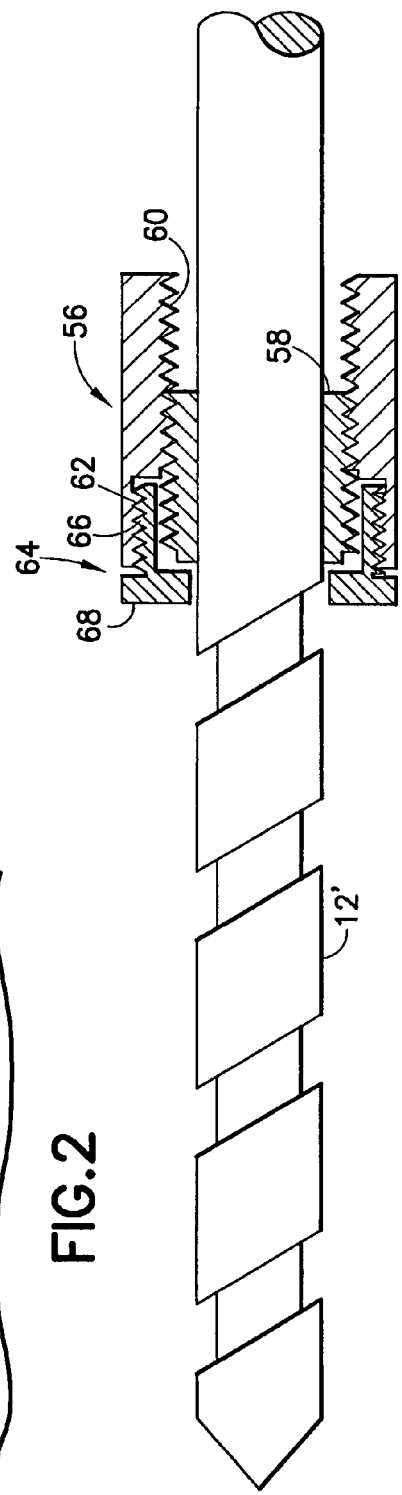

SLEEVED STOP FOR A DRILL BIT

BACKGROUND OF THE INVENTION

1. Field of the Invention

This invention is directed to the field of hardware for use with drills, and, more particularly, to a sleeved stop for a drill bit.

2. Description of Related Art

Drills are common hand tools. They are used in many applications, from home repair to surgery. One common problem associated with the use of drills is that it may be difficult to identify the desired depth of a hole being drilled. In some applications, such as installing door hinges, attaching legs to a table, or during surgery (e.g., dental surgery, neurosurgery, orthopedic surgery, or maxillofacial surgery), drilling the hole to a precise depth is of crucial importance, and so precise control of the depth of penetration of the drill bit is essential.

In simple applications, crude means have existed for providing a stop for the drill bit. In carpentry, for example, it is common to provide a visual stop for a drill bit by applying a long piece of masking tape to the exterior of the bit itself, whereby the edge of the tape closest to the tip of the drill is aligned with the desired maximum depth of penetration of the bit. The tape can also be wrapped about the bit several times to establish a shoulder which abuts the surface into which the drill penetrates. This functions to limit the travel of the bit beyond the desired depth. While this approach works satisfactorily in carpentry, it is not appropriate, for example, in oral surgery, where a more precise (and sanitary) form of stop is needed.

The prior art includes many known stops for drill bits. For example, U.S. Pat. No. 5,078,552 (Albel) shows a stop for a drill bit for regulating the depth to which a drill bit may extend. The stop is friction-fit to the exterior of a standard drill bit, and may be secured in place by securing the end of the bit to the drill. The stop, however, does not provide any means for finely controlling the precise depth to which the bit may extend.

Another known stop is shown in U.S. Pat. No. 5,152,792 (Watkins, et al.) which shows a sleeved stop to limit the depth of penetration of the bit. The stop is threaded and may be set to the desired depth but it does not provide a means of fine adjustment, as the threads are widely spaced. Alternatively, if the threads are finely spaced, coarse movements would be difficult, since many turns of the thread would be required to move the stop larger distances.

U.S. Pat. No. 4,710,075 (Davison) shows a stop for a surgical drill bit, in which the depth of penetration is limited by a frusto-conical stop attached to the exterior of the drill bit. The top of the drill bit (i.e., the part farthest from the tip of the bit) includes a series of parallel grooves, with which a plunger (set screw) engages to secure the stop against movement. This suffers from the drawback that the adjustment of the depth of the hole to be drilled is limited by the distance between the grooves. The depth cannot be adjusted, for example, to one-half the distance between adjacent grooves, as the plunger will not be engaged and would therefore be subject to movement.

Accordingly, there is a need in the art for a drill bit stop which provides means for reliably and precisely setting the depth of penetration of a drill bit, while preserving ease of use and adjustment for making both coarse and fine adjustments to the drilling depth.

SUMMARY OF THE INVENTION

In accordance with a preferred embodiment of the invention, there is provided a stop for a drill bit which includes at least one sleeve threadedly mounted to the exterior of the drill bit, for adjusting the depth of penetration of the drill bit into a surface, by positioning a shoulder of the stop so that it limits maximum penetration of the bit into or past the surface. The bit may include indicia for visually indicating the position of the shoulder with respect to the tip of the drill bit.

In accordance with a preferred embodiment of the invention, there is provided a stop for a drill bit which provides means for both coarse and fine adjustment of the depth of penetration of the drill bit into a surface, by positioning a shoulder of the stop so that it limits the maximum depth of penetration of the bit. Preferably, the adjustment is provided by two concentric sleeves, each co-axial with the bit. One of the sleeves, preferably the inner sleeve, provides the coarse adjustment, and may include first indicia for visually indicating the coarse position of the shoulder relative to the tip of the drill bit. The other sleeve, preferably the outer sleeve, provides the fine adjustment, and may include second indicia for visually indicating the fine position of the shoulder with respect to the tip of the drill bit.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings:

FIG. 2 is a detail of the exterior of the embodiment of FIG. 1;

FIG. 3 a partial cross-section of an alternate embodiment of the invention;

FIG. 4 is a partial cross-section of a further alternate embodiment of the invention;

FIG. 8 is a partial cross section of the embodiment of FIG. 6 with a deformable elastomer.

DETAILED DESCRIPTION OF THE PREFERRED EMBODIMENTS

Figure 1:
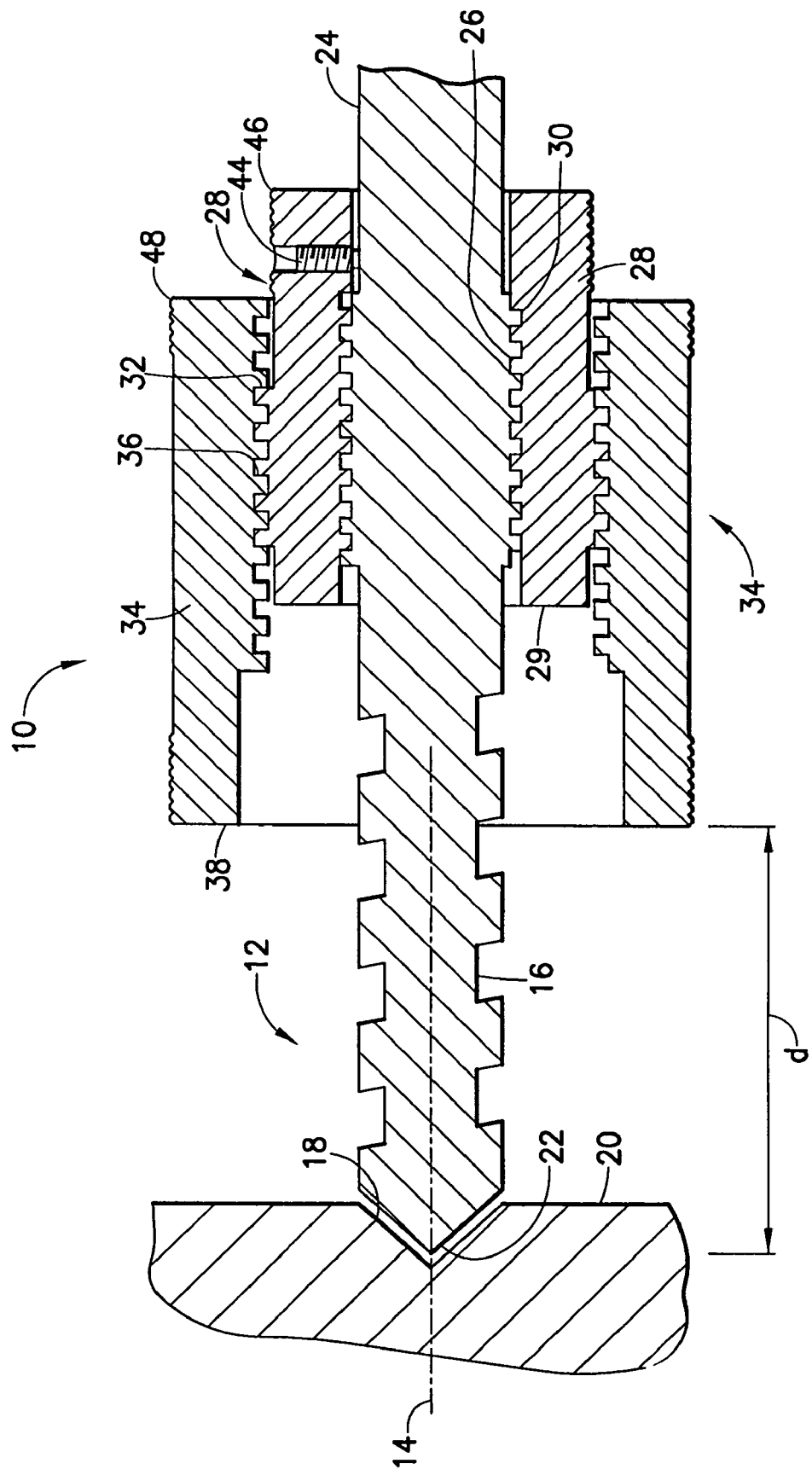
FIG. 1 is a cross-section of a preferred embodiment of the invention.

In FIG. 1 there is shown a stop 10 for a drill bit 12 in accordance with a preferred embodiment of the invention. Bit 12 is intended for use with a drill (not shown) which may be either electric or manual (such as, for example, an auger or gimlet). In accordance with standard practice, bit 12 is removably mounted in the drill for rotational movement about an axis 14 (shown in dashed line). Bit 12 includes a helical cutting groove 16 for drilling a hole 18 in a surface 20.

As is conventional, bit 12 includes a tip 22, and an opposed end 24. A threaded area 26 is provided between the tip 22 and end 24 on the exterior of bit 12. Stop 10 includes a first inner sleeve 28 engageable with bit 12, and rotatable about axis 14. Inner sleeve 28 includes an inner threaded area 30 and an outer threaded area 32. The inner threaded area has threading dimensioned to engage threaded area 26 of bit 12. Stop 10 further includes a second outer sleeve 34 which is engageable with inner sleeve 28, and is also rotatable about axis 14. Outer sleeve 34 includes inner threading 36 dimensioned for engaging outer threaded area 32 of inner sleeve 28. An edge of outer sleeve 34 proximate the tip 22 of the drill bit 12 forms a shoulder surface 38 which provides a drill bit stop as explained below.

The threads of inner threaded area 30 of inner sleeve 28 and threaded area 26 of bit 12 have a first pitch, while the threads of inner threaded area 36 of outer sleeve 34 and outer threaded area 32 of inner sleeve 28 have a second pitch. The first and second pitches may be equivalent or different, and are set so that one of the first and second pitches establishes a coarse adjustment thread, while the other pitch is set to establish a fine adjustment thread. As used herein, "coarse" and "fine" are relative terms, so that "coarse" axial movement of any element means axial movement which is a multiple of the axial movement per complete revolution of the element compared to the "fine" axial movement. By way of example, and not limitation, one revolution of the "coarse" adjustment may constitute a length of axial travel along axis 14 of ten times the length of travel of the "fine" adjustment, for one revolution about axis 14. It may also be possible to configure the relative turns of the threads so that a single turn of either or both of the sleeves corresponds to a specific depth of penetration of the drill bit. For example, and not in limitation, one complete turn of the "coarse" adjustment may cause movement of the stop of precisely one-sixteenth of an inch, while one complete turn of the "fine" adjustment may cause movement of the stop of precisely one sixty-fourth of an inch. The relative movement of the "coarse" and "fine" adjustments is purely a matter of design choice, and would depend upon the needs of the particular application.

The sleeved stop 10 can be used to engage the drill bit 12 either when the drill bit is attached to, or separated from, a drill. For example, if drill bit 12 is attached to a drill, the stop 10 will be coupled about the drill bit, in a manner explained more fully below, by insertion of the drill bit through the stop via drill bit tip 22. However, if the drill bit is detached from a drill, the stop 10 can be coupled to the drill bit via either tip 22 or end 24.

In use, the user would determine the maximum depth d of hole 18 and position the drill bit 12 into the stop 10 and adjust the stop so that shoulder 38 is at an approximate distance d as measured between shoulder 38 and the tip 22 of the bit 12. This is accomplished by placing the concentric inner and outer sleeves 28, 34 about either end of the drill bit 12, i.e. either tip 22 or end 24, and then rotating the inner sleeve 28 until inner threaded area 30 engages threaded area 26 on the drill bit 12. If the sleeve 28 is coupled to the drill bit 12 at the tip 22, the drill bit 12 will require a configuration wherein the diameter of the drill bit about threaded area 26 is larger than the diameter at cutting groove 16 so that the inner sleeve 28 can pass over, and not be obstructed by, cutting groove 16. Thereby, inner sleeve 28 can then engage threaded area 26. Once threaded area 26 of the drill bit 12 is engaged by inner threaded area 30 of inner sleeve 28, the inner sleeve 28 will then be rotated so that its leading edge 29 is positioned at a desired distance along the drill bit length. Thereafter, outer sleeve 34 can be rotated with respect to inner sleeve 28 for fine-tune adjustment of the position of shoulder 38, to precisely define the distance d.

In accordance with one embodiment, the threaded area 26 on the drill bit can be eliminated and the helical cutting groove can be used for threaded coupling to the threading 30 on the inner sleeve 28. Thus, once the stop 10 is in place on the bit 12, an appropriate amount of the cutting groove 16 will be exposed to drill a hole to a desired depth in surface 20.

To facilitate the positioning of shoulder 38, it is preferred that stop 10 include two sets of indicia, coarse indicia 40 and fine indicia 42, as seen in FIG. 2. Indicia 40 and 42 may be disposed on bit 12 and inner sleeve 28, respectively, so that movement of inner sleeve 28 along bit 12 will reveal the axial position of inner sleeve 28 with respect to tip 22, while movement of outer sleeve 34 along inner sleeve 28 will reveal the axial position of outer sleeve 34 with respect to inner sleeve 28. Either inner sleeve 28 or outer sleeve 34 may perform the "coarse" adjustment of stop 10, while the outer sleeve performs the "fine" adjustment, as a matter of design choice. It is preferred, however, that inner sleeve 28 perform the coarse adjustment while outer sleeve 34 perform the fine adjustment. It is also preferred that one or both of inner sleeve 28 and outer sleeve 34 include means for securing them in place relative to each other or to drill bit 12, such as, for example, a set screw 44 or other known anchoring devices.

In a preferred embodiment, each sleeve 28, 34 includes means for gripping that sleeve, for example by use of knurled surfaces 46, 48, respectively. It would also be possible to employ a projection, such as an arm 50 (FIG. 3) on one or both of inner sleeve 28 and outer sleeve 34, to facilitate rotational movement thereof.

To assist in the independent movement of inner sleeve 28 with respect to outer sleeve 34, it is preferred that inner sleeve 28 have an upper portion 52 (FIG. 2) which extends beyond the upper end 54 of outer sleeve 34 even when outer sleeve 34 is at its maximum distance away from tip 22. By gripping the upper portion 52, inner sleeve 28 may be rotated, which will simultaneously rotate outer sleeve 34 so that the relative positions of the inner and outer sleeves will remain unchanged.

An alternate arrangement of the coarse and fine adjustment mechanism of the invention is illustrated in FIG. 4. In this arrangement, a first sleeve 56 is mounted to an engagement region 58 of a drill bit 12'. First sleeve 56 has two different interior threads: a first thread 60 which engages engagement region 58, and a second thread 62 positioned on a stepped surface relative to the first thread 60. First sleeve 56 is mounted over second sleeve 64, the latter of which has an exterior thread 66 which engages second thread 62 of first sleeve 56. Second sleeve 64 further includes a shoulder 68 to act as a stop for the penetration of drill bit 12'. Threads 60 and 62 have different pitches, so that, for example, first thread 60 may provide coarse adjustment of the position of shoulder 68 and second thread 62 may provide fine adjustment of the position of shoulder 68. In one embodiment, the pitch of first thread 60 is roughly three times the pitch of second thread 62, so that one complete turn of first sleeve 56 on drill bit 12' equals three complete turns of second sleeve 64 within first sleeve 56.

Figure 5:
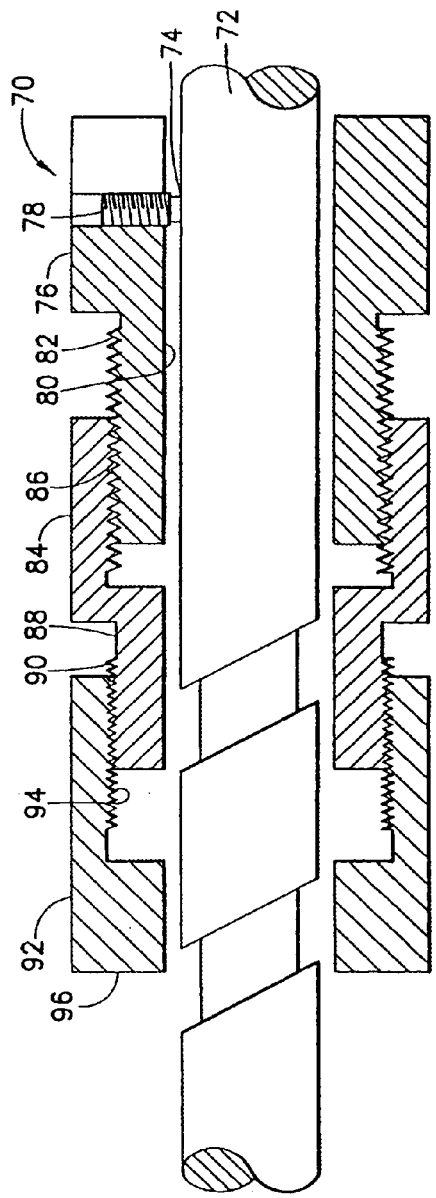
FIG. 5 is a partial cross-section of a still further alternate embodiment of the invention.

A still further alternate embodiment of the invention is shown in FIG. 5. In this embodiment, a stop 70 may be retrofitted to attach to a conventional drill bit 72, which has a smooth shank 74. An engagement threading 76 is mounted on shank 74 by a set screw 78, to prevent movement of engagement threading 76 relative to drill bit 72. Engagement threading 76 has a smooth interior surface 80 which slides over shank 74 to a desired location, and a threaded outer portion 82.

Stop 70 further includes a first sleeve 84, having a first thread 86 on the interior thereof, configured to mate with the thread of threaded outer portion 82. First sleeve 84 further includes a reduced diameter portion 88, having a second thread 90 on the exterior thereof. The pitch of second thread 90 is different from that of first thread 86. A second sleeve 92 is rotatably mounted to first sleeve 84, and has a thread 94 configured to mate with second thread 90 of first sleeve 84. Second sleeve 92 also includes a shoulder 96 which is configured to abut the surface into which drill bit 72 drills, when drill bit 72 reaches the desired depth, and thereby limit the penetration of drill bit 72 into the surface.

In operation, stop 70 functions much as stop 10 of FIG. 1, except that it has a reduced profile, resulting from the mounting of second sleeve 92 on reduced diameter portion 88 of first sleeve 84.

Figure 6:
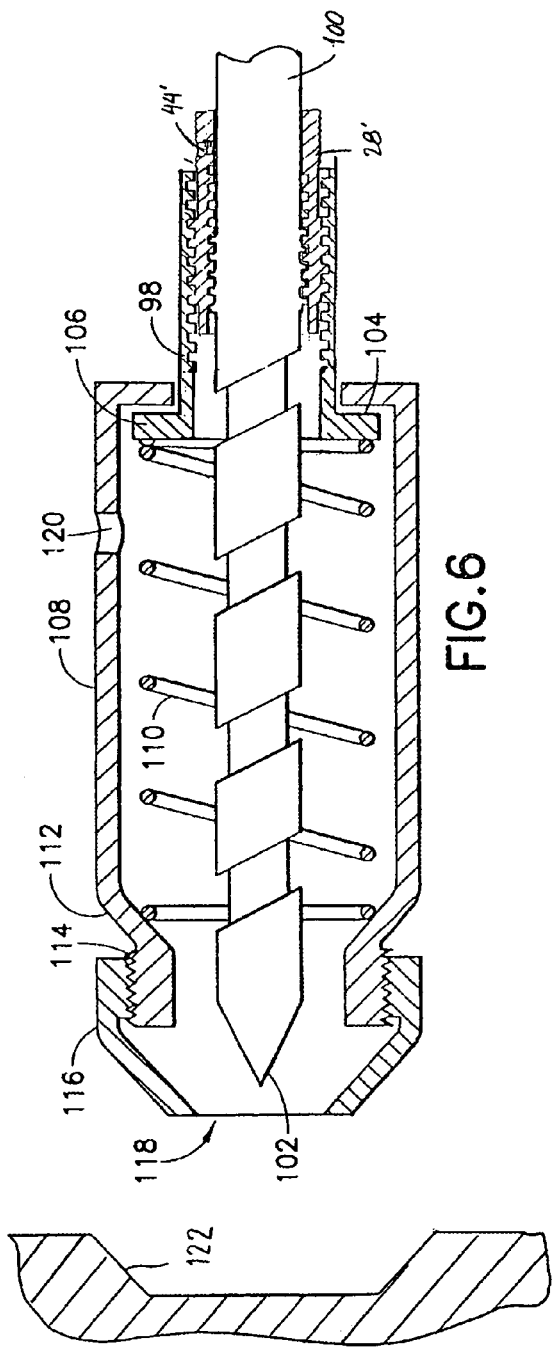
FIG. 6 is a partial cross-section of an additional feature of the invention.
Figure 7B:
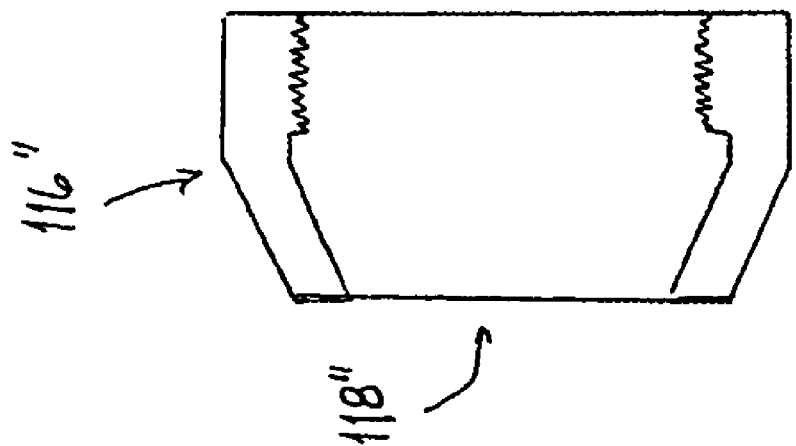
FIG. 7a and 7b are partial cross-sections of two different sized alignment piece from the embodiment of FIG. 6.
Figure 7A:
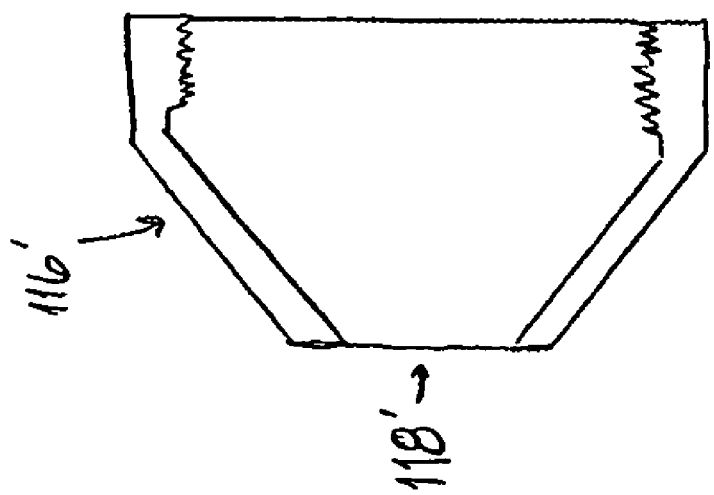
Figure 6:
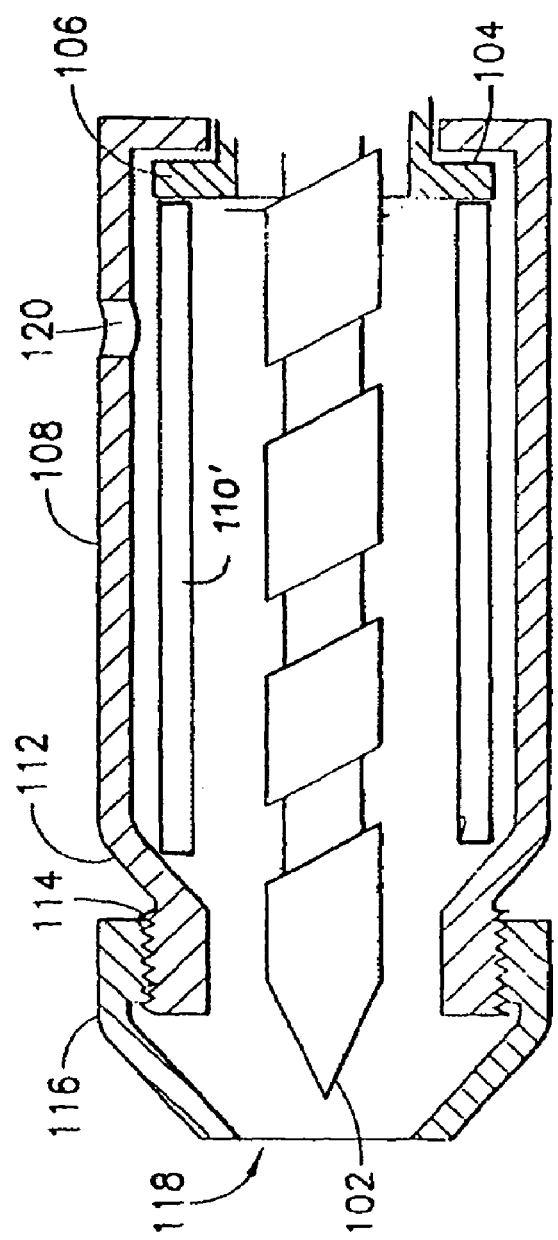

A further feature of a preferred embodiment of the invention is shown in FIG. 6. An outer sleeve 98 is mounted to a drill bit 100 having a tip 102. Outer sleeve 98 is mounted to drill bit 100 similarly to the mounting of outer sleeve 34 to drill bit 12 in FIG. 1. Outer sleeve 98 has an inner threaded area that is engaged with an outer threaded area of inner sleeve 28'. An inner threaded area of inner sleeve 28' threadably engages an outer threaded area on drill bit 100. A set screw 44 may be used to hold inner sleeve 28' on drill bit 100. Outer sleeve 98 and inner sleeve 28' are adjustable in the same manner as outer sleeve 34 and inner sleeve 28 of FIG. 1. Outer sleeve 98 includes an annular shoulder 104 projecting outwardly therefrom at an end 106 of outer sleeve 98 closest to tip 102 of drill bit 100. A centering sleeve 108 is mounted to end 106, so that centering sleeve 108 projects toward tip 102. A resilient member, such as a deformable elastomer 110' (see FIG. 8) or a spring 110 is mounted within centering sleeve 108 to bias centering sleeve 108 in a position fully extended over tip 102. Centering sleeve 108 includes a reduced diameter portion 112 having a threaded end 114 opposite end 106 of outer sleeve 98, proximate tip 102. A removable frusto-conical alignment piece 116 is threadedly mounted to threaded end 114. Alignment piece 116 has an aperture 118 therein, sized to accommodate the diameter of drill bit 100, by allowing the easy passage therethrough of drill bit 100. Differently sized alignment pieces 116 having differently sized apertures 118 may be used to accommodate drill bits of different diameters. For example, FIGS. 7a and 7b show an alignment piece 116' with an aperture 118' that is smaller than the aperture 118" of alignment piece 116".

A vent 120 in the side of centering sleeve 108 may be provided, to allow debris from the hole being drilled to exit centering sleeve 108, rather than accumulate therein.

Alignment piece 116 is centered on centering sleeve 108, so that it may engage a countersink 122 in the surface into which drill bit 100 drills. The angling of the sides of alignment piece 116 will automatically place tip 102 of drill bit 100 in the center of any countersink. When the user begins to place pressure on the rear of the drill, drill bit 100 will move towards the countersink 122, causing centering sleeve 108 to retract over outer sleeve 98 until spring 110 is fully compressed, thereby limiting the depth of penetration of drill bit 100 into the surface by stopping the forward progress of drill bit 100, indicating to the user that the drilling is complete. In this instance, the depth of penetration of drill bit 100 will be the depth corresponding to the position of shoulder 106, plus the minimum length of spring 110 (i.e., its length when fully compressed), plus the length of alignment piece 116. Thus, when setting the position of outer sleeve 98 to limit the depth of penetration of drill bit 100 into the surface into which it is drilling, these distances must be accounted for, either by labeling indicia (not shown) disposed on outer sleeve 98 or through otherwise informing the user of the need to account for the difference, as through a written instruction manual.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

For example, it will be appreciated by one of ordinary skill in the art that a single sleeve may be employed to adjust a depth of penetration of the drill bit, where the particular application does not call for the use of both coarse and fine adjustment.

What is claimed is:

1. A stop for a drill bit, said drill bit having an elongate body rotatable about an axis, a tip at one end of said body for drilling into a surface, a second end of said body opposed to said tip for coupling said bit to a drill, and an engagement region on the exterior of said body between said tip and said second end, said stop comprising:

a first sleeve for adjusting a position of said stop relative to said tip of said drill bit, said first sleeve having a first thread adapted to engage said engagement region on said drill bit, and a second thread having a pitch different from that of said first thread, said first sleeve being rotatably mounted to said drill bit about said engagement region, said first sleeve providing one of fine adjustment and coarse adjustment of said position of said stop with respect to said drill bit tip; and a second sleeve concentrically coupled to said first sleeve for adjusting said position of said stop relative to said tip of said drill bit, said second sleeve having a thread adapted to engage said second thread of said first sleeve, said second sleeve being rotatably mounted to said first sleeve, said second sleeve also providing the other of fine adjustment and coarse adjustment of said position of said stop;

a centering member for centering said drill bit in a predetermined drilling location in said surface, said centering member being retractably mounted to said drill bit and projecting from said drill bit towards said surface, said centering member including a forward end;

a resilient member disposed within said centering member, to bias said centering member towards a fully extended position in which said forward end of said centering member extends past said tip of said drill bit; and a shoulder, mounted on one of said second sleeve or said centering member, for limiting a depth of penetration of said drill bit into said surface.

2. The stop of claim 1 wherein said resilient member is a spring.

3. The stop of claim 1 wherein said resilient member is a resilient elastomer.

4. The stop of claim 1 wherein said forward end of said centering member has threads; and wherein said stop further comprises an alignment piece having threads on one end thereof and an aperture on an opposed end thereof, said threads of said alignment piece being configured to mate with said threads of said centering member, and said aperture being sized to accommodate the maximum diameter of said drill bit.

5. The stop of claim 4, wherein said alignment piece has a frusto-conical exterior, where said aperture is disposed at the smaller end of the frustum of said frusto-conical exterior, and said threads of said alignment piece are disposed at the opposite end of said frustum.

6. The stop of claim 4, further comprising a plurality of alignment pieces, each having an aperture having a different size, to accommodate drill bits having a plurality of different diameters.

7. The stop of claim 1, wherein said predetermined drilling location includes a countersink bore below said surface, and said centering member is adapted to center said drill bit in said countersink bore for drilling into said surface.

* * * * *